(12) United States Patent
Wang et al.

(10) Patent No.: US 9,052,307 B2
(45) Date of Patent: Jun. 9, 2015

(54) METHOD FOR FABRICATING BIOSENSOR

(71) Applicants: Tsinghua University, Beijing (CN); HON HAI PRECISION INDUSTRY CO., LTD., New Taipei (TW)

(72) Inventors: Xue-Shen Wang, Beijing (CN); Qun-Qing Li, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 29 days.

(21) Appl. No.: 13/943,753

(22) Filed: Jul. 16, 2013

(65) Prior Publication Data

US 2013/0298394 A1 Nov. 14, 2013

Related U.S. Application Data

(63) Continuation of application No. 13/008,146, filed on Jan. 18, 2011, now Pat. No. 8,512,533.

(30) Foreign Application Priority Data

Oct. 27, 2010 (CN) .......................... 2010 1 0521439

(51) Int. Cl.
*B05D 5/12* (2006.01)
*G01N 33/50* (2006.01)
*B82Y 15/00* (2011.01)
*G01N 27/327* (2006.01)
*C23C 16/26* (2006.01)
*B82Y 30/00* (2011.01)

(52) U.S. Cl.
CPC ........... *G01N 33/50* (2013.01); *Y10T 29/49002* (2015.01); *Y10T 29/49121* (2015.01); *C23C 16/26* (2013.01); *B05D 5/12* (2013.01); *B82Y 15/00* (2013.01); *G01N 27/3275* (2013.01); *G01N 27/3278* (2013.01); *B82Y 30/00* (2013.01)

(58) Field of Classification Search
USPC .............................. 427/58, 122; 977/742, 924
See application file for complete search history.

(56) References Cited

U.S. PATENT DOCUMENTS

| | | | |
|---|---|---|---|
| 7,927,651 B2 * | 4/2011 | Hong et al. | 427/10 |
| 8,512,533 B2 * | 8/2013 | Wang et al. | 204/403.01 |
| 2006/0078468 A1 * | 4/2006 | Gabriel et al. | 422/88 |
| 2006/0204428 A1 | 9/2006 | Noy et al. | |
| 2009/0035469 A1 | 2/2009 | Sue et al. | |
| 2010/0260745 A1 * | 10/2010 | Zhou et al. | 424/130.1 |

* cited by examiner

*Primary Examiner* — Brian K Talbot
(74) *Attorney, Agent, or Firm* — Novak Druce Connolly Bove + Quigg LLP

(57) ABSTRACT

A method for fabricating a plurality of biosensors includes the steps of: providing a base with a surface; forming a carbon nanotube array including a plurality of carbon nanotubes substantially parallels to each other on the surface; forming a plurality of lead pairs on the surface, the plurality of lead pairs divides the plurality of carbon nanotubes into a plurality of first carbon nanotubes and a plurality of second carbon nanotubes; eliminating the plurality of second carbon nanotubes; cutting the plurality of first carbon nanotubes to form a plurality of third carbon nanotubes and a plurality of fourth carbon nanotubes; and fabricating a plurality of receptors to electrically connect the plurality of third carbon nanotubes to the plurality of fourth carbon nanotubes.

15 Claims, 9 Drawing Sheets

METHOD FOR FABRICATING BIOSENSOR

RELATED APPLICATIONS

This application is a continuation application of U.S. patent application Ser. No. 13/008,146, filed Jan. 18, 2011, with U.S. Pat. No. 8,512,533, entitled, "BIOSENSOR, BIOSENSOR PACKAGE STRUCTURE HAVING SAME, AND METHOD FOR FABRICATING SAME," which claims all benefits accruing under 35 U.S.C. §119 from China Patent Application No. 201010521439.0, filed on 2010 Oct. 27, in the China Intellectual Property Office.

BACKGROUND

1. Technical Field

The present disclosure relates to a biosensor with electrodes comprising a plurality of carbon nanotubes, a biosensor package structure having the same, and a method for fabricating the same.

2. Description of Related Art

In general, a biosensor is a device that uses a specific biological element or a physical element similar to the biological element to get information from a measured object. The detected information is usually transduced by the biosensor into recognizable signals such as colors, fluorescence, or electrical signals. With technical advances in modem science, a biosensor is one of the devices that have developed rapidly.

A biosensor is composed of a receptor which reacts with a measured object to be detected, and electrodes which transmit current variation generated by the reaction between the receptor and the measured object. Examples of the receptor include an enzyme, antibody, antigen, membrane, receptor, cell, tissue, and deoxyribonucleic acid (DNA), which selectively reacts with the measured object. The electrodes are usually metal electrodes.

However, a width of each of the metal electrodes in the above-described biosensor is in a range from several micrometers (um) to dozens of micrometers. Thus, an amount of electrodes in a unit area of the biosensor is too few to influence accuracy and sensitivity of the same. Furthermore, the metal electrodes with poor inoxidability will shorten a lifetime of the biosensor.

Thus, there remains a need for providing a new biosensor which has greater accuracy, sensitivity, and a longer lifetime.

BRIEF DESCRIPTION OF THE DRAWINGS

Many aspects of the disclosure can be better understood with reference to the drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
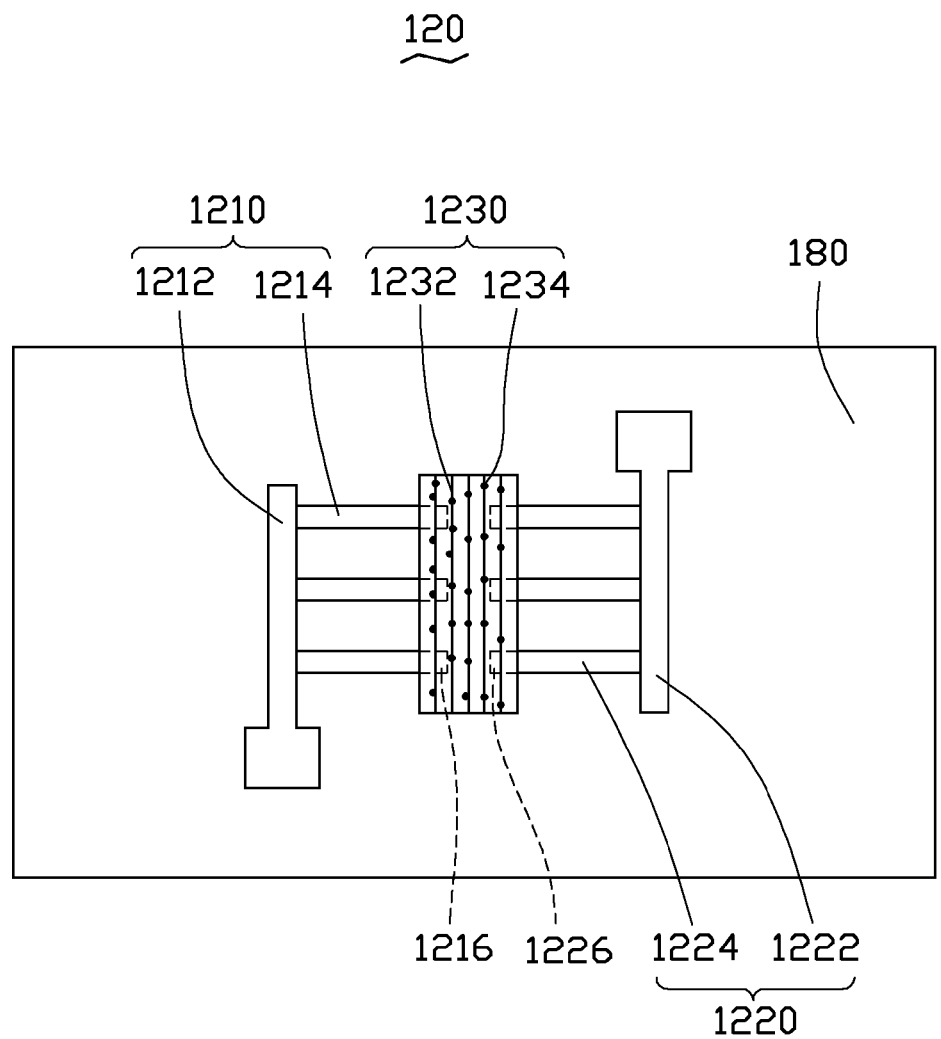
FIGS. 1, 2, and 3 are schematic views of embodiments of a biosensor.

According to one embodiment, a biosensor 120 as illustrated in FIG. 1 comprises a base 180 with a surface, two electrodes 1210 and 1220, and a receptor 1230. The two electrodes 1210 and 1220 are illustrated as a first electrode 1210 and a second electrode 1220 for exemplification and should not be treated as a limitation. The first electrode 1210, the second electrode 1220, and the receptor 1230 are located on the surface of the base 180 with an interval.

The first electrode 1210 comprises a first lead 1212 and a plurality of first carbon nanotubes 1214. The first carbon nanotubes 1214 are substantially parallel to each other, and comprise a first probe 1216. The first lead 1212 is electrically connected to one side of each of the first carbon nanotubes 1214 and an external circuit (not shown).

Similarly, the second electrode 1220 comprises a second lead 1222 and a plurality of second carbon nanotubes 1224. The second carbon nanotubes 1224 are substantially parallel to each other, and comprise a second probe 1226. The second lead 1222 is electrically connected to one side of each of the second carbon nanotubes 1224 and an external circuit (not shown).

The first carbon nanotubes 1214 and the second carbon nanotubes 1224 can be single-walled carbon nanotubes, double-walled carbon nanotubes, multi-walled carbon nanotubes, or combinations thereof. The diameter of the single-walled carbon nanotubes can be in the range from about 0.5 nanometers (nm) to about 50 nm. The diameter of the double-walled carbon nanotubes can be in the range from about 1 nm to about 50 nm. The diameter of the multi-walled carbon nanotubes can be in the range from about 1.5 nm to about 50 nm. In one embodiment, the length of the first carbon nanotubes 1214 and the second carbon nanotubes 1224 can be in a range from about 10 micrometers (um) to about 50 um.

More specifically, the first carbon nanotubes 1214 respectively correspond to the second carbon nanotubes 1224. Thus, the first probe 1216 of each of the first carbon nanotubes 1214 corresponds to the second probe 1226 of each of the second carbon nanotubes 1224. A distance between each two first carbon nanotubes 1214 is in a range from about 5 um to about 10 um. Similarly, a distance between each two second carbon nanotubes 1224 is in a range from about 5 um to about 10 um. A distance between the first probe 1216 of each of the first carbon nanotubes 1214 and the second probe 1226 of each of the second carbon nanotubes 1224 is equal to or less than 10 um. Furthermore, as shown in FIG. 1, an extended direction of each of the first carbon nanotubes 1214 is substantially parallel to an extended direction of each of the second carbon nanotubes 1224.

The first lead 1212 and the second lead 1222 can be conductive thick liquid, metal, carbon nanotubes, indium tin oxide (ITO), or any combination thereof. In one embodiment, the first lead 1212 and the second lead 1222 are made by printing or plating the conductive thick liquid. The conductive thick liquid comprises powdered metal, powdered glass with a low fusion point, and binder. The powdered metal is powdered silver. The binder is terpineol or ethyl cellulose. A weight percentage of the powdered metal is in a range from about 50% to about 90%. A weight percentage of the powdered glass with a low fusion point is in a range from about 2% to about 10%. A weight percentage of the binder is in a range from about 8% to about 40%.

The receptor 1230 comprises a plurality of carriers 1232 and a plurality of sensing materials 1234. The sensing materials 1234 are embedded in each of the carriers 1232. The first probe 1216 of each of the first carbon nanotubes 1214 and the second probe 1226 of each of the second carbon nanotubes 1224 are covered by the receptor 1230, such that the first electrode 1210 and the second electrode 1220 are electrically connected to each other. More specifically, the carriers 1232 define a plurality of conductive circuits, between the first carbon nanotubes 1214 of the first electrode 1210 and the second carbon nanotubes 1224 of the second electrode 1220, to electrically connect the sensing materials 1234.

The carriers 1232 can be carbon nanotubes, carbon fibers, amorphous carbon, graphite, or any combination thereof. In one embodiment, the carriers 1232 are carbon nanotubes with a plurality of functional groups. The functional groups can be carboxyl (—COOH) groups, hydroxyl (—OH) groups, aldehyde (—CHO) groups, amino (—NH2) groups, or any combination thereof.

In testing, the sensing materials 1234 embedded in the carriers 1232 react to a measured object such that current of the biosensor 120 is varied. The current variation of the biosensor 120 is transmitted by the first carbon nanotubes 1214 and the first lead 1212. Alternatively, the current variation of the biosensor 120 is transmitted by the second carbon nanotubes 1224 and the second lead 1222. The sensing materials 1234 can be antibodies, antigens, DNA, or any combination thereof. In one embodiment, the sensing materials 1234 are antibodies.

Figure 2:
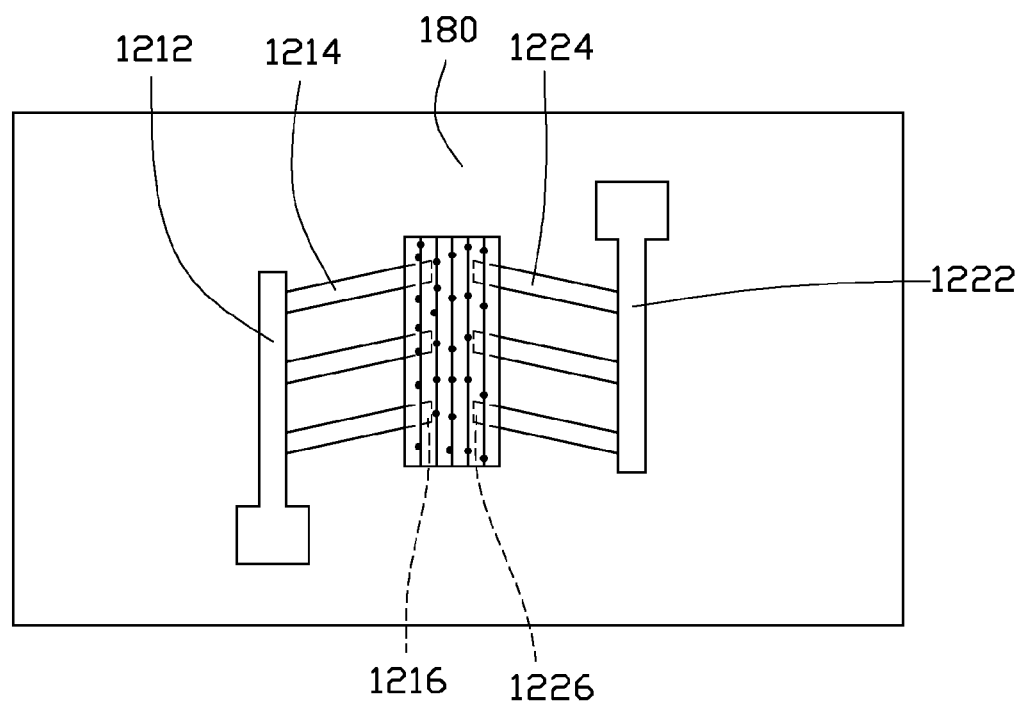

According to another embodiment, a biosensor 120 as illustrated in FIG. 2 comprises a base 180 with a surface, a first lead 1212, a plurality of first carbon nanotubes 1214, a second lead 1222, and a plurality of second carbon nanotubes 1224. Each of the first carbon nanotubes 1214 comprises a first probe 1216, and each of the second carbon nanotubes 1224 comprises a second probe 1226. Furthermore, as shown in FIG. 2, the first carbon nanotubes 1214 substantially parallel to each other and the second carbon nanotubes 1224 substantially parallel to each other form a specific angle.

Figure 3:
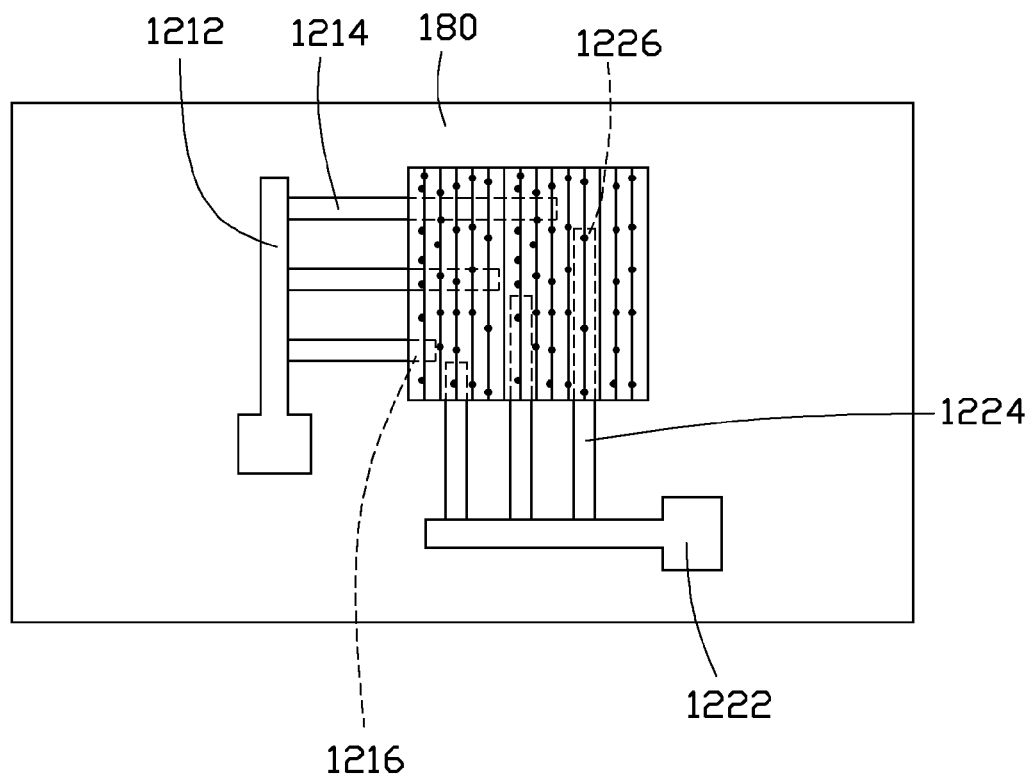

According to still another embodiment, a biosensor 120 as illustrated in FIG. 3 comprises a base 180 with a surface, a first lead 1212, a plurality of first carbon nanotubes 1214, a second lead 1222, and a plurality of second carbon nanotubes 1224. Each of the first carbon nanotubes 1214 comprises a first probe 1216, and each of the second carbon nanotubes 1224 comprises a second probe 1226. Furthermore, as shown in FIG. 3, an extended direction of each of the first carbon nanotubes 1214 is substantially perpendicular to an extended direction of each of the second carbon nanotubes 1224.

Figure 4:
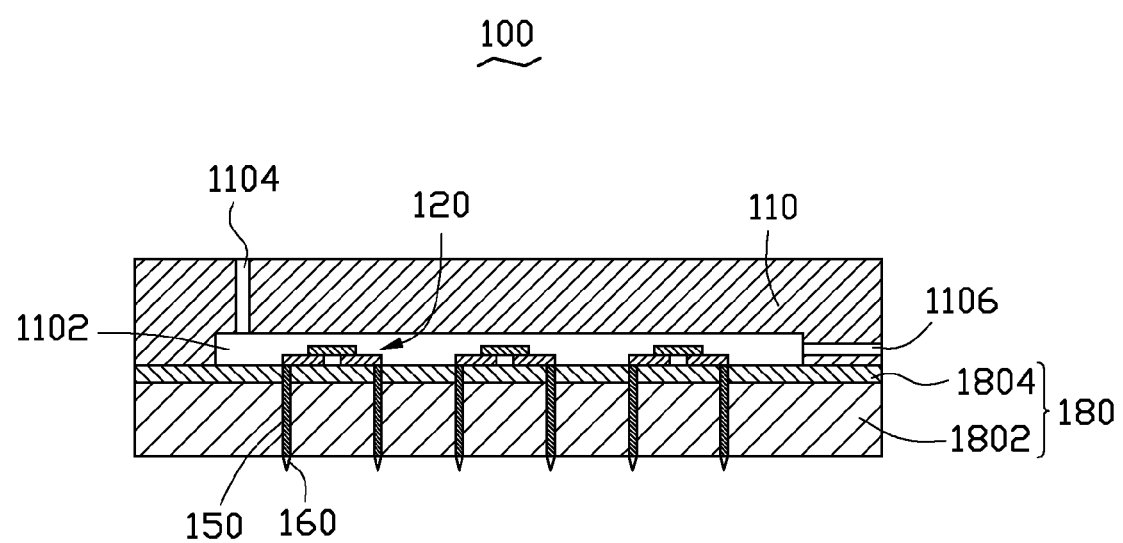
FIG. 4 is a schematic view of an embodiment of a biosensor package structure.

According to an embodiment, a biosensor package structure 100 as illustrated in FIG. 4 comprises a base 180 with a surface, a cover box 110, and a plurality of biosensors 120. The base 180 and the cover box 110 are plastered to each other to define a cavity 1102.

The base 180 which comprises conductive wires 150 can be a hard base or a flexible base. The hard base can be a ceramic base, a glass base, a quartziferous base, a siliceous base, an oxidative siliceous base, a diamond base, an alumina base, or any combination thereof. The flexible base can be a macromolecule base made by polydimethylsiloxane (PDMS), polycarbonate (PC), polymethyl methacrylate (PMMA), polyethylene (PE), polyimide (PI), polyethylene terephthalate (PET), polyether sulphone (PES), cellulose resin, polyvinylchloride (PVC), benzocyclobutene (BCB), acrylic resin, or any combination thereof. The base 180 comprises a siliceous slice 1802 with a surface and a silica layer 1804 formed on the surface of the siliceous slice 1802. In one embodiment, a thickness of the siliceous slice 1802 is in a range from about 0.5 millimeter (mm) to about 2 mm, and a thickness of the silica layer 1804 is in a range from about 100 um to about 500 um.

The cover box 110 comprises an input passage 1104 and an output passage 1106. The input passage 1104 is disposed in one side of the cover box 110, and the output passage 1106 is disposed in an opposite side of the same. In the embodiment, the cover box 110 is a poly dimethyl siloxane (PDMS) box. Diameters of the input passage 1104 and the output passage 1106 is in a range from about 200 um to about 400 um. The cavity 1102 is defined as a cuboid, a length of the cavity 1102 is in a range from about 5 mm to about 10 mm, a width of the same is in a range from about 0.2 mm to about 1 mm, and a height of the same is in a range from about 50 um to about 100 um.

The biosensors 120 are located on the surface of the base 180 side by side. The first electrode 1210 and the second electrode 1220 of each of the biosensors 120 are connected to pins 160 by the conductive wires 150. Thus, the biosensors 120 are electrically connected to the external circuit via the pins 160.

Accordingly, when the measured object is delivered to the cavity 1102 by the input passage 1104, and withdrawn from the cavity 1102 by the output passage 1106, the measured object will pass through the biosensors 120. Thus, the biosensors 120 react to the measured object such that current of each of the biosensors 120 is varied. Afterward, the current variation of each of the biosensors 120 is transmitted to the external circuit by the conductive wires 150 and the pins 160. Finally, the external circuit can get information from the measured object.

According to an embodiment, a method for fabricating a plurality of biosensors is illustrated in following steps. For exemplary purpose, the embodiment is adapted for fabricating the biosensors 120 of FIG. 1.

Figure 5:
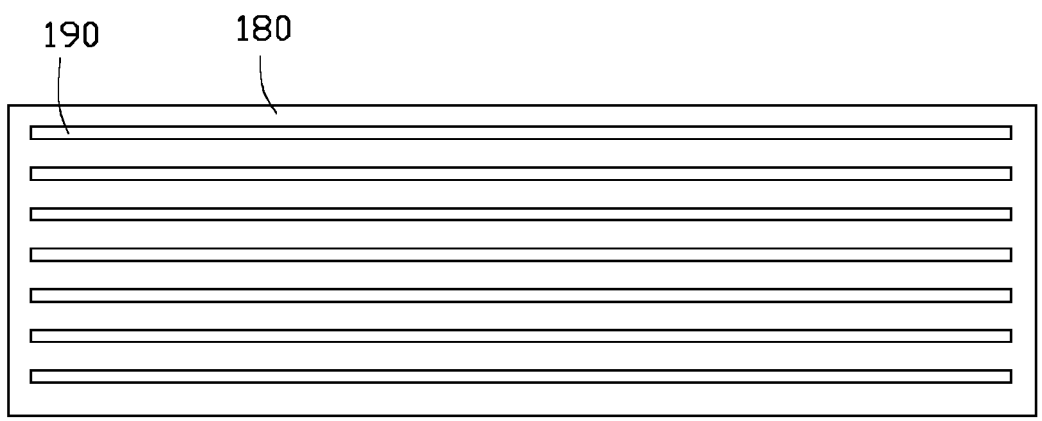
FIGS. 5, 6, 7, 8, and 9 show different schematic views of processes to manufacture a plurality of biosensors.

Referring to FIG. 5, in step one, a base 180 with a surface is provided, and a carbon nanotube array 190 is formed on the surface of the base 180. The carbon nanotube array 190 comprises a plurality of carbon nanotubes substantially parallel to each other.

Figure 6:
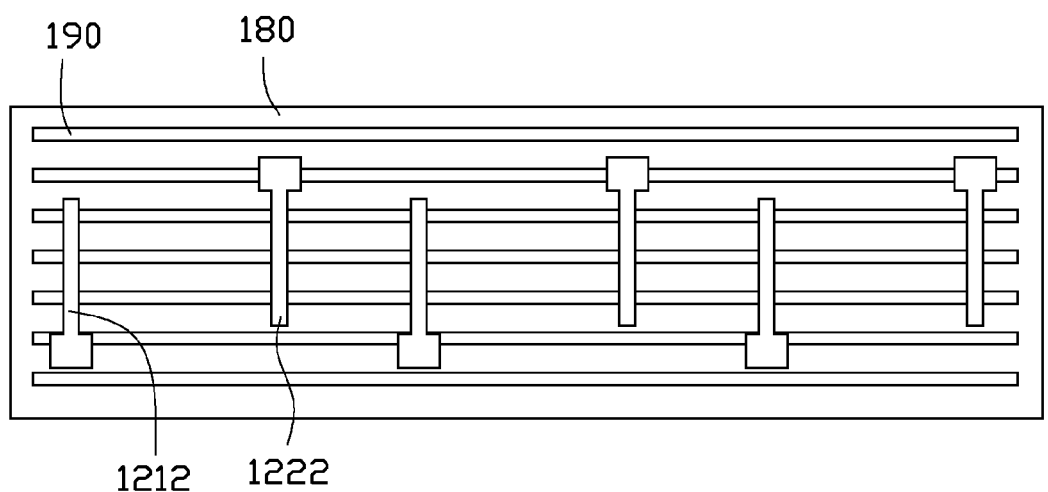

Referring to FIG. 6, in step two, a plurality of first leads 1212 and a plurality of second leads 1222 are formed by printing or plating conductive thick liquid on the surface of the base 180. Each of the first leads 1212 corresponds to each of the second leads 1222, and are electrically connected to each other by at least one of the carbon nanotubes of the carbon nanotube array 190.

Figure 7:
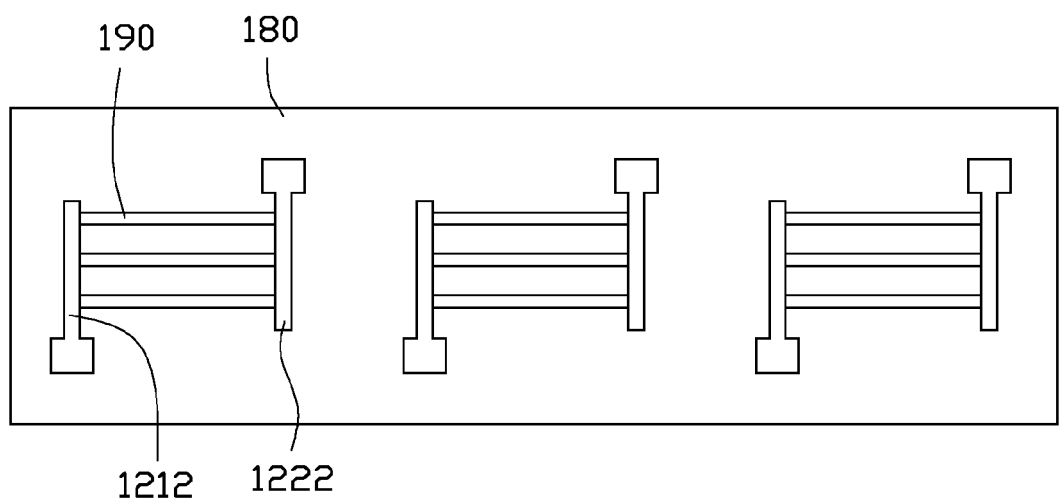

Referring to FIG. 7, in step three, a part of the carbon nanotubes of the carbon nanotube array 190 is eliminated. Thus, the carbon nanotubes between each of the first leads 1212 and each of the second leads 1222 remain on the surface of the base 180.

Figure 8:
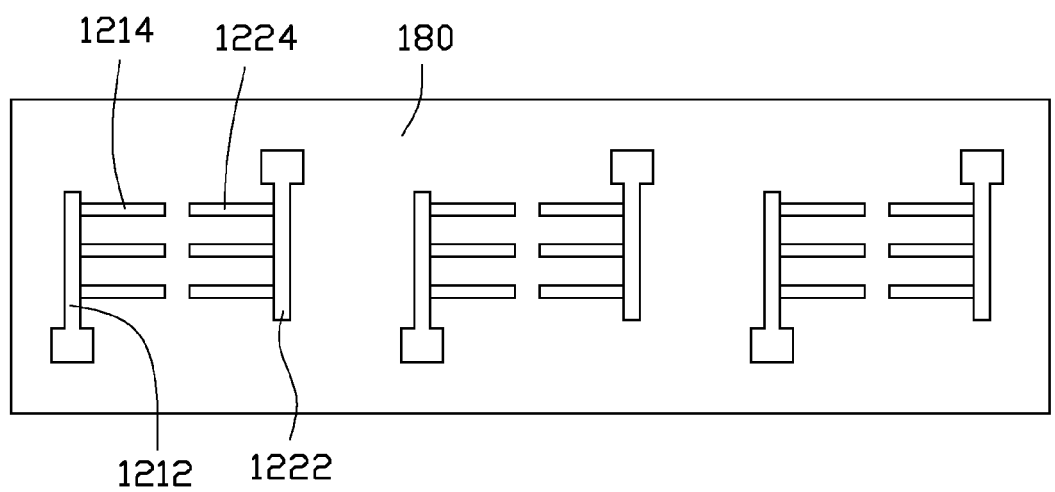

Referring to FIG. 8, in step four, the carbon nanotubes between each of the first leads 1212 and each of the second leads 1222 are cut to form a plurality of first carbon nanotubes 1214 and a plurality of second carbon nanotubes 1224. Each of the first carbon nanotubes 1214 corresponds to each of the second carbon nanotubes 1224.

Figure 9:
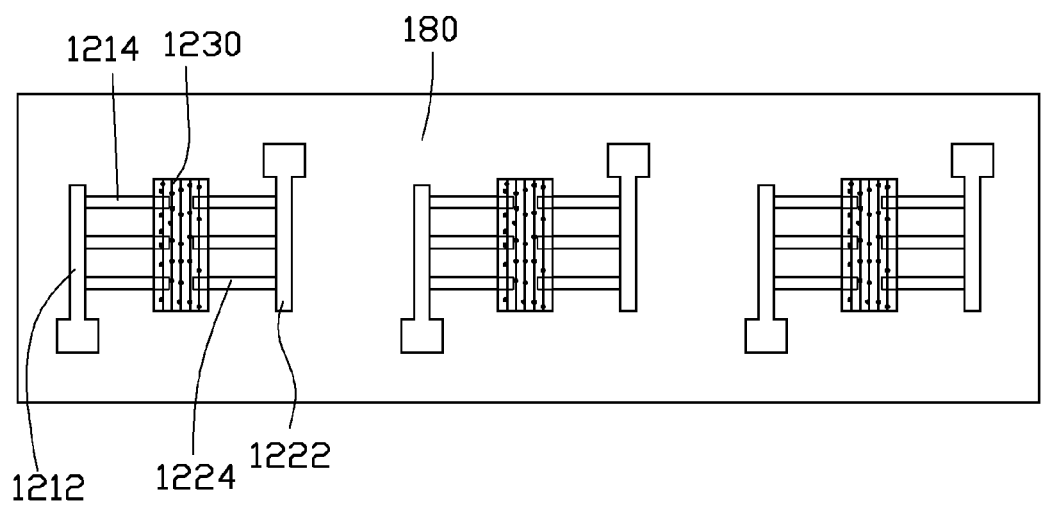

Referring to FIG. 9, in step five, receptors 1230 are fabricated between each of the first leads 1212 and each of the second leads 1222. Thus, the first carbon nanotubes 1214 and the second carbon nanotubes 1224 between each of the first leads 1212 and each of the second leads 1222 are electrically connected to each other by one of the receptors 1230.

Accordingly, the present disclosure is capable of transmitting current variation of a biosensor via electrodes with carbon nanotubes. In addition, a width each of the electrodes can be decreased without influencing the accuracy and sensitivity of the biosensor. Thus, the biosensor can be easily manufactured with greater accuracy, sensitivity, and a longer lifetime.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

What is claimed is:

1. A method for fabricating a plurality of biosensors, comprising:
   providing a base with a surface;
   forming a carbon nanotube array comprising a plurality of carbon nanotubes substantially parallels to each other on the surface;
   forming a plurality of lead pairs on the surface, wherein each lead pair comprises a first lead and a second lead separately configured with the first lead, the plurality of lead pairs divides the plurality of carbon nanotubes into a plurality of first carbon nanotubes and a plurality of second carbon nanotubes, the plurality of first carbon nanotubes is located in the plurality of lead pairs, and the plurality of second carbon nanotubes is located out of the plurality of lead pairs;
   eliminating the plurality of second carbon nanotubes;
   cutting the plurality of first carbon nanotubes to form a plurality of third carbon nanotubes and a plurality of fourth carbon nanotubes; and
   fabricating a plurality of receptors to electrically connect the plurality of third carbon nanotubes to the plurality of fourth carbon nanotubes.

2. The method as claimed in claim 1, wherein the forming a carbon nanotube array comprises a plurality of carbon nanotubes substantially parallels to each other on the surface the plurality of carbon nanotubes are parallel to the surface.

3. The method as claimed in claim 1, wherein the forming a carbon nanotube array comprises a plurality of carbon nanotubes substantially parallels to each other on the surface a distance between each two carbon nanotubes is in a range from about 5 um to about 10 um.

4. The method as claimed in claim 1, wherein the forming a plurality of lead pairs on the surface the plurality of lead pairs is formed by printing or plating a conductive thick liquid on the surface.

5. The method as claimed in claim 4, wherein the forming a plurality of lead pairs on the surface the conductive thick liquid comprises a powdered metal, a powdered glass, and a binder.

6. The method as claimed in claim 5, wherein the forming a plurality of lead pairs on the surface a weight percentage of the powdered metal is in a range from about 50% to about 90%, a weight percentage of the powdered glass is in a range from about 2% to about 10%, and a weight percentage of the binder is in a range from about 8% to about 40%.

7. The method as claimed in claim 5, wherein the forming a plurality of lead pairs on the surface the powdered metal is powdered silver, and the binder is terpineol or ethyl cellulose.

8. The method as claimed in claim 1, wherein the forming a plurality of lead pairs on the surface the first lead and the second lead in each of the plurality of lead pairs are electrically connected by at least one of the plurality first carbon nanotubes.

9. The method as claimed in claim 1, wherein the cutting the plurality of first carbon nanotubes to form a plurality of third carbon nanotubes and a plurality of fourth carbon nanotubes the plurality of third carbon nanotubes is electrically connected to the first lead, and the plurality of fourth carbon nanotubes is electrically connected to the second lead.

10. The method as claimed in claim 1, wherein the fabricating a plurality of receptors to electrically connect the plurality of third carbon nanotubes to the plurality of fourth carbon nanotubes each of the plurality of receptors is located in the plurality of lead pairs.

11. The method as claimed in claim 1, wherein the fabricating a plurality of receptors to electrically connect the plurality of third carbon nanotubes to the plurality of fourth carbon nanotubes each of the plurality of receptors comprises a plurality of carriers and a plurality of sensing materials.

12. The method as claimed in claim 11, wherein the fabricating a plurality of receptors to electrically connect the plurality of third carbon nanotubes to the plurality of fourth carbon nanotubes the plurality of carriers is selected from the group consisting of carbon nanotubes, carbon fibers, amorphous carbon, and graphite.

13. The method as claimed in claim 11, wherein the fabricating a plurality of receptors to electrically connect the plurality of third carbon nanotubes to the plurality of fourth carbon nanotubes the plurality of sensing materials is selected from the group consisting of antibodies, antigens, and DNA.

14. The method as claimed in claim 1, wherein the eliminating the plurality of second carbon nanotubes the eliminating process is carried out by a laser.

15. The method as claimed in claim 1, wherein the cutting the plurality of first carbon nanotubes to form a plurality of third carbon nanotubes and a plurality of fourth carbon nanotubes the cutting process is carried out by a laser.

* * * * *